(12) United States Patent
Meister et al.

(10) Patent No.: US 8,944,987 B2
(45) Date of Patent: Feb. 3, 2015

(54) CARDIAC ASSISTANCE DEVICE AND METHOD FOR THE CONTROL THEREOF

(75) Inventors: Markus Meister, Munich (DE); Stephen M. Wildhirt, Munich (DE)

(73) Assignee: Adjucor UG, Munich (DE)

( * ) Notice: Subject to any disclaimer, the term of this patent is extended or adjusted under 35 U.S.C. 154(b) by 374 days.

(21) Appl. No.: 13/393,420

(22) PCT Filed: Sep. 30, 2010

(86) PCT No.: PCT/EP2010/005947
§ 371 (c)(1),
(2), (4) Date: Jul. 27, 2012

(87) PCT Pub. No.: WO2011/038904
PCT Pub. Date: Apr. 7, 2011

(65) Prior Publication Data
US 2012/0283506 A1   Nov. 8, 2012

(30) Foreign Application Priority Data

Sep. 30, 2009   (DE) .......................... 10 2009 043 795

(51) Int. Cl.
*A61M 1/12* (2006.01)
*A61M 1/10* (2006.01)

(52) U.S. Cl.
CPC ............. *A61M 1/1068* (2013.01); *A61M 1/106* (2013.01); *A61M 2205/15* (2013.01); *A61M 2230/30* (2013.01)
USPC ............................................. 600/17; 600/16

(58) Field of Classification Search
USPC ....................................... 600/16, 17
See application file for complete search history.

(56) References Cited

U.S. PATENT DOCUMENTS

| | | | |
|---|---|---|---|
| 3,053,249 | A | 9/1962 | Smith |
| 5,490,820 | A | 2/1996 | Schock |
| 5,749,839 | A | 5/1998 | Kovacs |
| 6,126,590 | A | 10/2000 | Alferness |
| 6,258,021 | B1 | 7/2001 | Wilk |
| 6,602,182 | B1 | 8/2003 | Milbocker |
| 6,626,821 | B1 | 9/2003 | Kung |
| 7,637,880 | B2 | 12/2009 | Ferrari |

(Continued)

FOREIGN PATENT DOCUMENTS

| | | | |
|---|---|---|---|
| DE | 69427906 T2 | 4/2002 | |
| EP | 1748809 B1 | 11/2008 | |

(Continued)

OTHER PUBLICATIONS

International Search Report from PCT/EP2010/005947, mailed Dec. 16, 2010, 4 pages.

(Continued)

*Primary Examiner* — Mark W Bockelman
(74) *Attorney, Agent, or Firm* — Fish & Richardson P.C.

(57) ABSTRACT

A cardiac assistance, device has a supporting component, which surrounds the heart and on the inside of which a plurality of adjacent inflatable and deflatable chambers are provided, via which an inside wall can be displaced inward. The chambers have a fluidic connection to at least one pump via lines. A plurality of supply valves on the supply side are arranged between the pump and the chambers. Some individual chambers or groups of chambers are assigned dedicated supply valves, in order to drive the chambers individually or in groups.

18 Claims, 8 Drawing Sheets

(56) References Cited

U.S. PATENT DOCUMENTS

| | | |
|---|---|---|
| 2002/0065449 A1 | 5/2002 | Wardle |
| 2003/0229260 A1 | 12/2003 | Girard |
| 2004/0102804 A1 | 5/2004 | Chin |
| 2004/0267329 A1 | 12/2004 | Raman et al. |
| 2005/0107661 A1 | 5/2005 | Lau et al. |
| 2006/0074484 A1 | 4/2006 | Huber |
| 2006/0217774 A1 | 9/2006 | Mower et al. |
| 2007/0270654 A1 | 11/2007 | Pignato |
| 2008/0021266 A1 | 1/2008 | Laham |
| 2008/0214888 A1* | 9/2008 | Ben Shalom |
| 2008/0319255 A1 | 12/2008 | Cohn |
| 2009/0036730 A1 | 2/2009 | Criscione et al. |
| 2010/0030017 A1 | 2/2010 | Baker |
| 2010/0152523 A1 | 6/2010 | MacDonald et al. |
| 2010/0160725 A1 | 6/2010 | Kiser |
| 2010/0256441 A1 | 10/2010 | Lu |
| 2011/0021864 A1 | 1/2011 | Criscione |
| 2012/0130485 A1 | 5/2012 | Lillehei |
| 2012/0142996 A1 | 6/2012 | Criscione |

FOREIGN PATENT DOCUMENTS

| | | |
|---|---|---|
| WO | WO9830271 A1 | 7/1998 |
| WO | WO0025842 A1 | 5/2000 |
| WO | WO2010042016 A1 | 4/2010 |

OTHER PUBLICATIONS

International Preliminary Report on Patentability and Written Opinion from PCT/EP2010/005947 issued Apr. 3, 2012, 8 pages.

Kaden, Malte, Examination Report for European Patent Application No. 10765952.6, dated Jan. 14, 2014, 5 pages.

European Search Report for European Patent Application No. 14150491, mailed Mar. 28, 2014, 5 pages.

Van Veen, Jennifer, Examination Report for European Patent Application No. 14150491 dated Apr. 11, 2014, 5 pages.

Porter, Jr., Gary A., USPTO Non-Final Office Action in U.S. Appl. No. 13/838,517, mailed May 23, 2014, 13 pages.

* cited by examiner

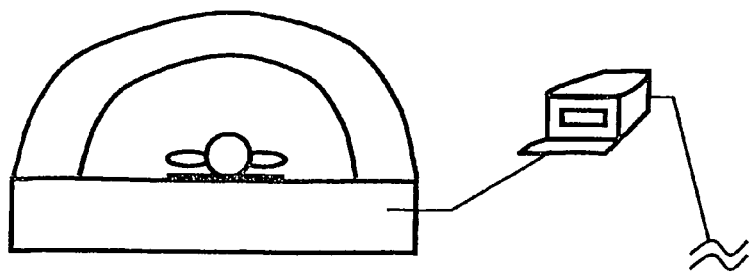
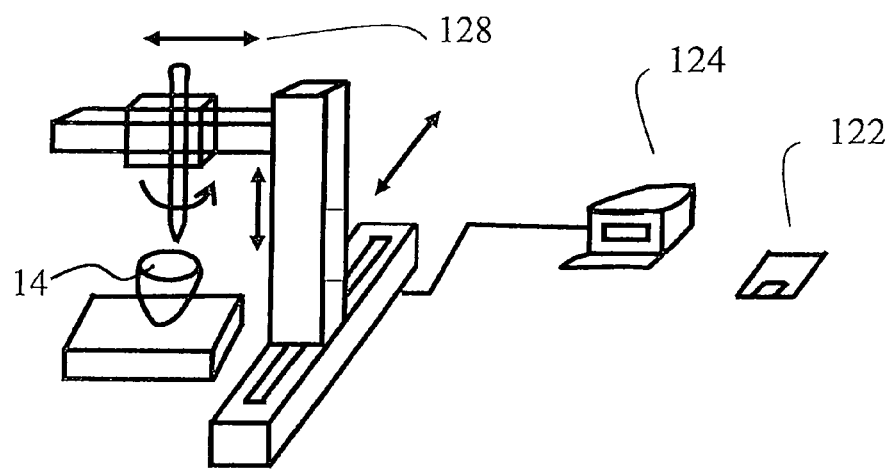
Fig. 9
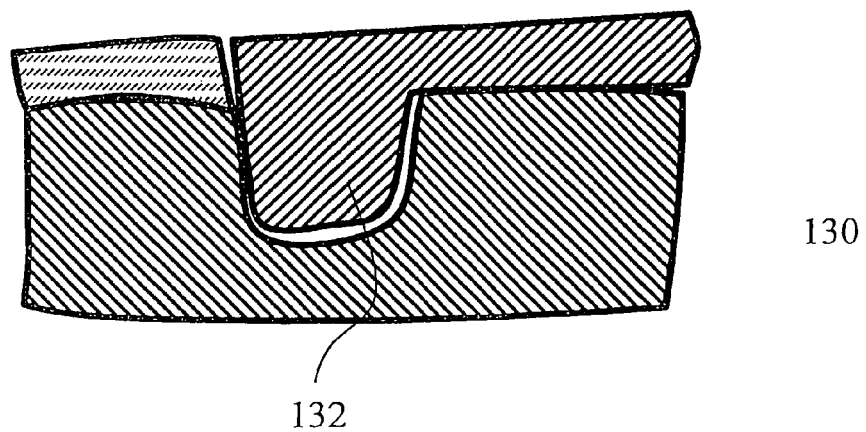
Fig. 10

CARDIAC ASSISTANCE DEVICE AND METHOD FOR THE CONTROL THEREOF

CROSS-REFERENCE TO RELATED APPLICATIONS

This application is tiled under 35 USC §371 as the U.S. national stage of International Application Number PCT/EP2010/005947. filed on Sep. 30, 2010, the entire contents of which are hereby incorporated by reference.

The invention relates to a cardiac assistance device and to a method for the control thereof.

BACKGROUND

The clinical picture of cardiac insufficiency (or heart failure) describes the state in which the heart is unable to provide a sufficient pumping force to supply the organism with blood. It is characterized by a clinical syndrome consisting of fatigue, shortness of breath and fluid retention. The causes are complex and are often related to lifestyle choices (risk factors) in the industrialized nations. Epidemiologically, the figures for the United States of America reveal the extent of the disease and can be fully ascribed to the seven most important medical and health markets (USA, France, Germany, Italy, Japan, Spain and England). It is generally assumed that some 23 million people worldwide suffer from cardiac insufficiency and that there are about 2 million new cases of the disease each year.

Some 5 million people presently suffer from cardiac insufficiency in the USA, with a rate of 550,000 new cases every year. In view of the rapidly ageing population, the next ten years will see the number of patients suffering from cardiac insufficiency double in each decade of life over the age of 50; that is to say, in the year 2018 a total of 10 million people in the USA will suffer from this disease and will require corresponding therapy.

In order to increase the life expectancy of the patient, it is not only possible to perform heart transplantation or the implantation of intravascular assistance systems, with the associated risks of stroke, hemorrhage or infections, but also to consider placing around the heart a sleeve or a bag comprising inflatable chambers. These chambers are filled and emptied according to the contraction of the heart, such that they press from outside against the heart and, during the contraction, completely or at least partially assist the heart by active compression or augmentation or even take over the action of the heart. The bag or the sleeve is as flexible as possible, in order to be able to adapt to the shape of the heart. An example of a cardiac assistance device of this kind is disclosed in EP 1 748 809 B1.

SUMMARY

An objective of the invention is to make available an efficient cardiac assistance device and to specify an optimized method for the production thereof.

In one aspect, the cardiac assistance device has a supporting component which surrounds the heart and on the inside of which a plurality of adjacent inflatable and deflatable chambers are provided, via which an inside wall can be displaced inward, wherein the chambers have a fluidic connection to at least one pump via lines. A plurality of supply valves are arranged on the supply side between pump and chambers. At least individual chambers or groups of chambers are assigned dedicated supply valves, in order to control the chambers independently, either individually or in groups. All of the chambers are preferably connected in parallel, such that they can be controlled individually or in groups. It is thus also possible to obtain chronologically staggered pressure profiles or different pressure profiles.

The preferably 1:1 assignment of chambers and supply valves may assist the heart in an exact manner, and the natural and sometimes very complex pumping movement of the heart may be simulated. Moreover, it is also possible to specifically assist damaged subregions of the heart. One aspect of the present invention proposes not only making available one supply valve for the plurality of chambers, but also permitting an individual control of the chambers, which is achieved using a multiplicity of supply valves. In this way, the diseased heart can be assisted on a much more individual basis, and it is possible to obtain a pumping action adapted to different load situations, since the chambers are filled to different degrees, and also with a time interval between each other. Moreover, individual regions of the heart can be assisted segmentally (regionally).

The chambers may be arranged asymmetrically.

At least one pressure accumulator is arranged on the supply side between the pump and the chambers, into which pressure accumulator the pump feeds pressure fluid, wherein the valves may be arranged downstream from the pressure accumulator. By provision of a pressure accumulator, the pump can be operated permanently at lower power, and pressure drops are avoided. The pressure accumulator means that sufficient pressure is permanently available to very rapidly inflate individual chambers or all of the chambers. In addition or as an alternative to this, a pressure fluid collection chamber can also be present upstream from the pump, and the lines leading from the individual chambers open into the pressure fluid collection chamber. The pressure fluid collection chamber serves as an intermediate store for fluid.

In a preferred embodiment, a pressure sensor is comprised to determine the pressure in the pressure accumulator. The data obtained via the pressure sensor make it possible to control the pump in a targeted manner if the pressure in the pressure accumulator is too high or too low. The pump can thus be maintained at a minimum speed of rotation, thereby saving energy.

The speed of rotation of the pump can be changed via the control system when the pressure in the pressure accumulator drops below a predefined minimum pressure or exceeds a predefined maximum pressure.

If a dedicated supply and discharge line issues from each chamber, i.e. is assigned only to this chamber, it is also possible to control the deflation individually for each chamber.

The chambers preferably have a direct fluidic connection to the pump on the discharge side, in order to ensure that the fluid is immediately pressurized again via the pump without substantial flow losses. This is also intended to keep the line length of the fluid circuit to a minimum.

It is advantageous if, on the discharge side between the chambers and the pump, discharge valves are provided, via which it is then possible to vary the duration for which the chambers remain inflated. In addition, the deflation of the chambers can also be chronologically staggered in this way.

In order to achieve more individual cardiac assistance, the discharge valves may also be assigned to individual chambers or groups of chambers.

In a space-saving embodiment of the invention, at least one supply and discharge valve, preferably all the supply and discharge valves assigned in each case to an individual chamber or to a group of chambers are in each case combined to form a multi-way valve.

According to one embodiment, the chamber-side supply line in part forms the discharge line. Consequently, the chambers themselves have only one common supply and discharge line, minimizing the space occupied by the device.

The device can be designed as a closed circuit, which lies completely inside the body or which is also positioned partially outside the body (e.g. pump or energy store). In another embodiment, provision is made for the device to be operated as an open system. This means that the device, downstream of the chambers, releases the compressed air to the outside via a line protruding from the body. If they are present, the discharge valves can still lie inside the body. The pump lying inside or outside the body sucks in air from the atmosphere.

A control system of the valves and an emergency sensor system coupled thereto mean that, when leakage from a chamber is detected, it is possible to permanently close the valves assigned to the defective chamber. Since the refilling of pressure fluid, or more generally of fluid, into the circuit is very complex or in some cases could only be done transcutaneously, even the very smallest leaks may be avoided.

The invention proposes, according to a preferred embodiment, that an additionally present emergency pump is activated as soon as a pump control system identifies the detection of a pump defect.

Flow or pressure sensors coupled to a control system for the valves and/or the pump make it possible to determine pressure in individual chambers or groups of chambers. The desired chamber pressure that is to be established can be controlled or even regulated using these valves. It is likewise possible to rapidly determine pressure drops, for example in the event of a leak.

According to the preferred embodiment, pressure sensors proximal to the heart side are also provided. They are coupled to a control system for valves and/or the pump and allow a conclusion to be drawn concerning the cardiac assistance that is provided by the device according to the invention and the cardiac assistance that is needed. In addition, by way of the sensors on the heart, the heart rate can also be adapted to the rate of the assistance device. However, this can also be achieved additionally or alternatively by an ECG or by coupling to a pacemaker, such as a twin-chamber pacemaker.

An intracorporeal refill tank for fluid, which can be coupled to the fluid circuit via a refill tank valve, permits the supply of fluid, in particular pressure fluid, into the fluid circuit if there is too little fluid present.

The refill tank is preferably made of metal (for example titanium), plastic or glass, or consists of a sandwich structure made of these materials.

In some embodiments, the refill tank valve is also coupled to a control system (in particular a central control system) or else could be controlled from outside the body. For example, data such as the maximum pressure in the chamber can be read out from outside the body, such that conclusions can be drawn concerning the amount of fluid located in the fluid circuit. In this way, for example, the necessary missing amount of fluid can be increased by the treating physician. This is preferably done from outside the body via transmitter/receiver units, via which the refill tank valve is briefly opened.

This refilling can also be effected completely automatically by a control system which, when fluid loss is detected, automatically drives the refill tank valve into the open position.

In other embodiments, a transcutaneously connectable refill site, in particular designed as a passive valve, could be present, in which case the coupling of the refill tool can be effected, for example, by a screw fastening or bayonet catch.

A central subcutaneous control system for the pump and the valves can have a receiver and can be designed to be reprogrammed via the receiver. In this way, the mode of operation of the device can be changed, for example on the basis of an altered disease profile. If the corresponding control system also has a transmitter for reading out data, the mode of operation of the cardiac assistance device can be determined from outside or, by way of the corresponding sensors, the performance of the heart can also be determined.

An extracorporeal control unit coupled wirelessly to the subcutaneous control system serves to capture and convey the data from the device. An Internet interface allows the data to be forwarded, possibly even "live", to a treating physician. The heart patient therefore does not have to personally consult the physician and can instead link up to the physician. The physician possibly has the advantage that data may be recorded and sent to him over quite a long period of time. This permits a more precise diagnosis of the state of health and monitoring of the mode of operation of the device according to the invention.

A diseased heart can also become smaller over the course of time. This would mean that the cardiac assistance device might become too large for the heart or it might no longer be optimally adapted to it. Such a decrease in the size of the heart could be inferred from a constantly reduced chamber pressure and/or blood pressure. The data are conveyed via pressure sensors for determining the chamber pressure and/or the blood pressure to the central control system for the pump and for the valves, which central control system evaluates the data. Above all, the way in which blood pressure and chamber pressure are measured is particularly advantageous. In the event that a decrease in the size of the heart is detected, the valves are actuated by the control system in such a way that the chambers are emptied less completely and/or hitherto unused chambers are filled. The cardiac assistance device is thus adapted to the smaller heart. This concept is preferably coupled to the parallel arrangement of the chambers.

Synchronization of the device to the heart can be achieved in particular if the central control system for the pump and for the valves is coupled to a pacemaker, in particular a twin-chamber pacemaker.

This central control system for the pump and the valves could also or additionally be coupled to an ECG.

These two options serve above all for the resynchronization of the heart action.

The cardiac assistance device according to one aspect of the invention has an inherently stiff supporting component, not a highly flexible one. The supporting component does not substantially yield during operation, with the result that the chambers can bear on the supporting component. By means of the stiff supporting component, the device can locally press against the heart wall in a targeted manner.

According to the preferred embodiment, the cardiac assistance device is a pneumatically operating device, i.e. the chambers are inflated using gas, in particular air.

Another asopect of the invention relates to a method of controlling a cardiac assistance device described herein, by at least one control system coupled to the valves. This control system controls the valves in groups or individually. In this way, it is possible to simulate the natural pumping movement of the heart. To this end, it can be advantageous if the chambers are filled/emptied with a time interval between each other.

To this end, according to the preferred embodiment, it can be advantageous to fill the lower chambers first, by means of the assigned supply valves being opened first. After a time interval, the superior chambers are then inflated. In this way, it is possible to assist the so-called lifting function of the heart in the direction of the aorta.

The speed of rotation of the pump may be changed as a function of values determined by flow sensors or pressure sensors in the fluid circuit and/or as a function of ECG values, when predefined values are exceeded or are not reached.

Generally, the pressure values could also be detected via flow sensors.

In the preferred embodiment, the cardiac assistance device is equipped with a cup-shaped supporting component into which the heart is fitted, and the supporting component lies in the pericardium. However, in other embodiments, the cup-shaped supporting component can also be arranged on the outside around the pericardium.

Further features and advantages of the invention will become clear from the following description and from the attached drawings, to which reference is made.

DESCRIPTION OF DRAWINGS

FIG. 9 shows a schematic view illustrating the production of the supporting component of the device.

FIG. 10 shows a schematic sectional view through an injection mold for producing the supporting component of the cardiac assistance device according to the invention.

DETAILED DESCRIPTION

Figure 1:
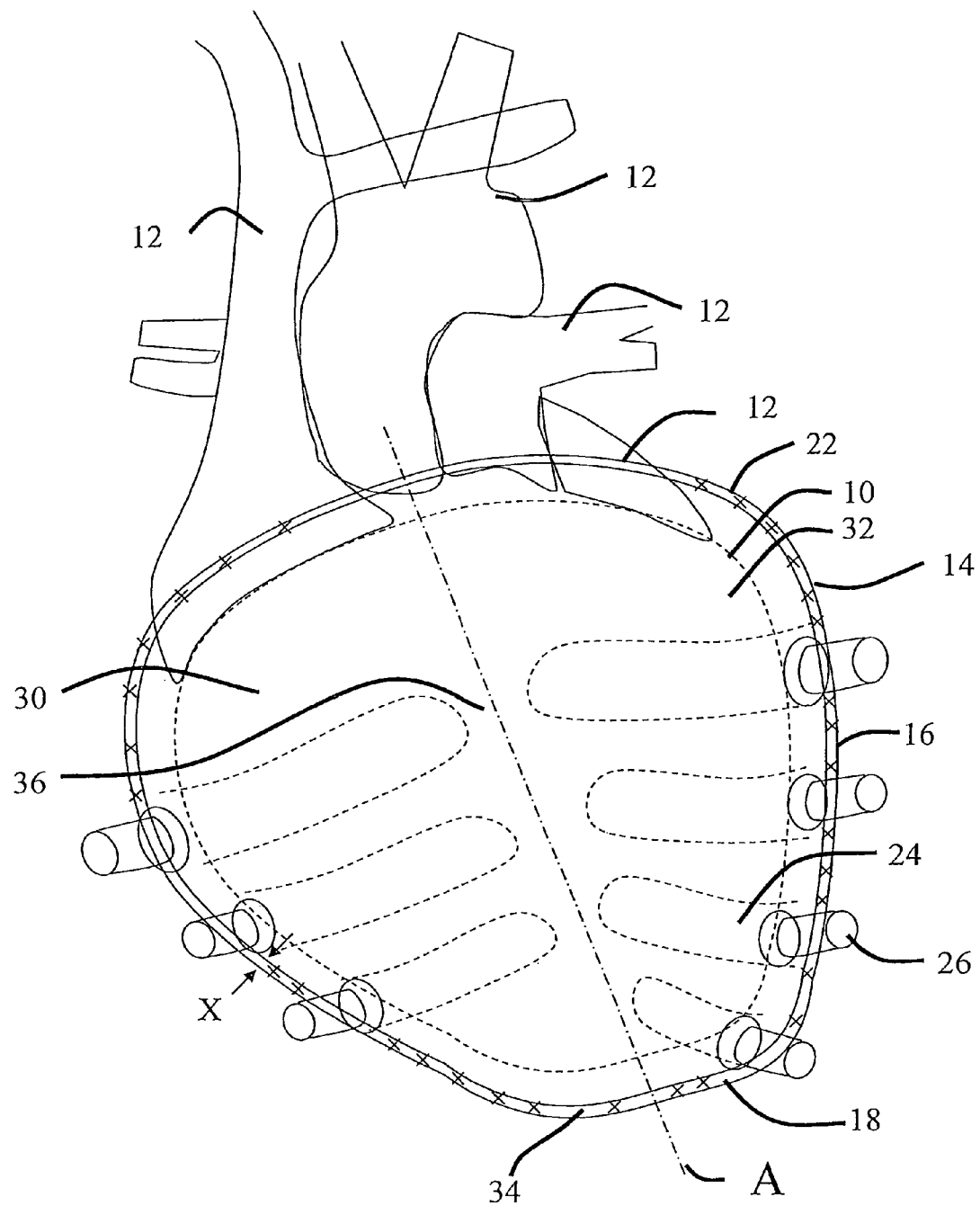
FIG. 1 shows a schematic view of the fitted cardiac assistance device.

FIG. 1 shows a schematic view of a human heart 10, which is indicated by broken lines and from which the known atria and major vessels 12 branch off.

An incompetent heart may only partialy perform its pump function, or indeed can no longer perform this function at all. To assist the pump function of the heart 10, a cardiac assistance device is present which has a cup-shaped supporting component 14 with a closed circumferential side wall 16 and with a bottom section 18. The supporting component 14 is open at the top. The corresponding opening bears the reference sign 20. The atria and major vessels 12 extend through this opening.

At the upper edge 38 of the supporting component 14, an axial holder 22, e.g. a cuff that has been welded on or molded on, extends inward. The heart 10 is inserted into the supporting component 14 from above through the opening 20, without being damaged in the process, and is surrounded by the supporting component 14. The axial holder 22 is preferably made flexible in order to permit easier insertion of the heart 10 and can thus be stretched outward during the insertion. For improved axial fixing, the axial holder 22 can be fixed on the pericardial reflection or on other points.

A plurality of adjacent chambers 24 is provided on the inner side of the supporting component 14. Each adjacent chamber 24 preferably has a dedicated connection line 26. To make matters clearer, only one of the numerous chambers 24 is provided with a reference sign in FIG. 1, along with its associated connection line 26.

Figure 8:
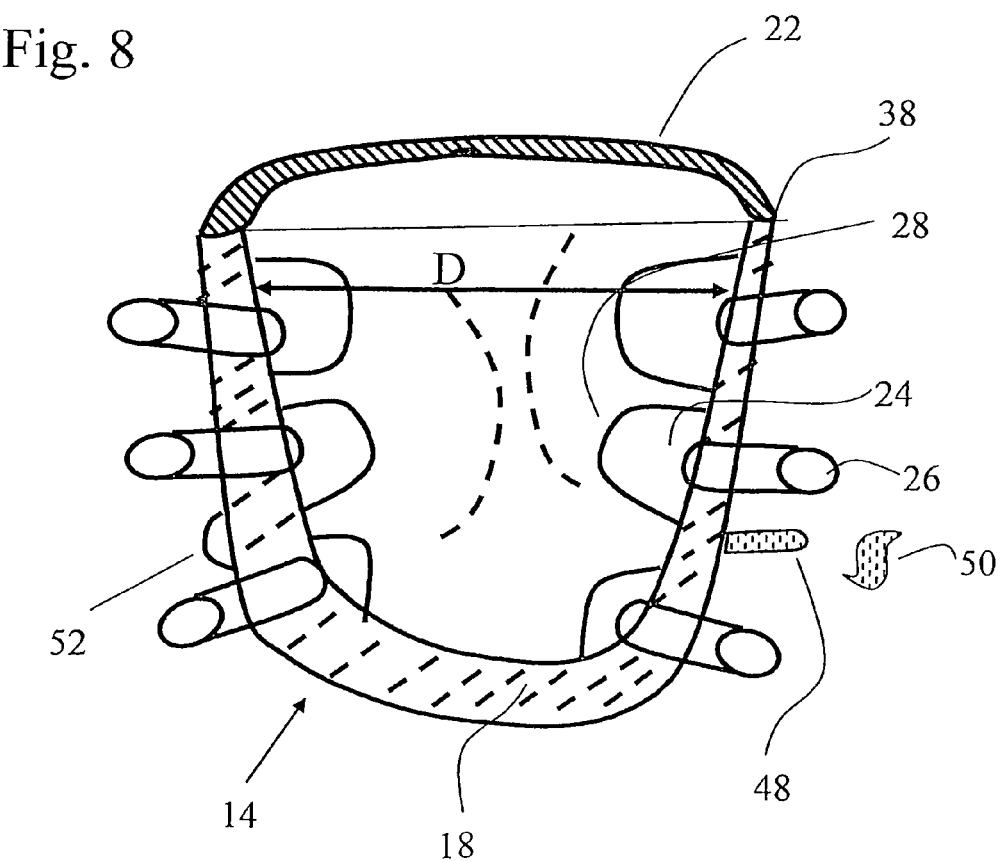
FIG. 8 shows a sectional view through the unit composed of supporting component and chambers according to another embodiment.

FIG. 8 shows the chambers 24 with their flexible and in particular elastic wall 28 on the inside.

Figure 4:
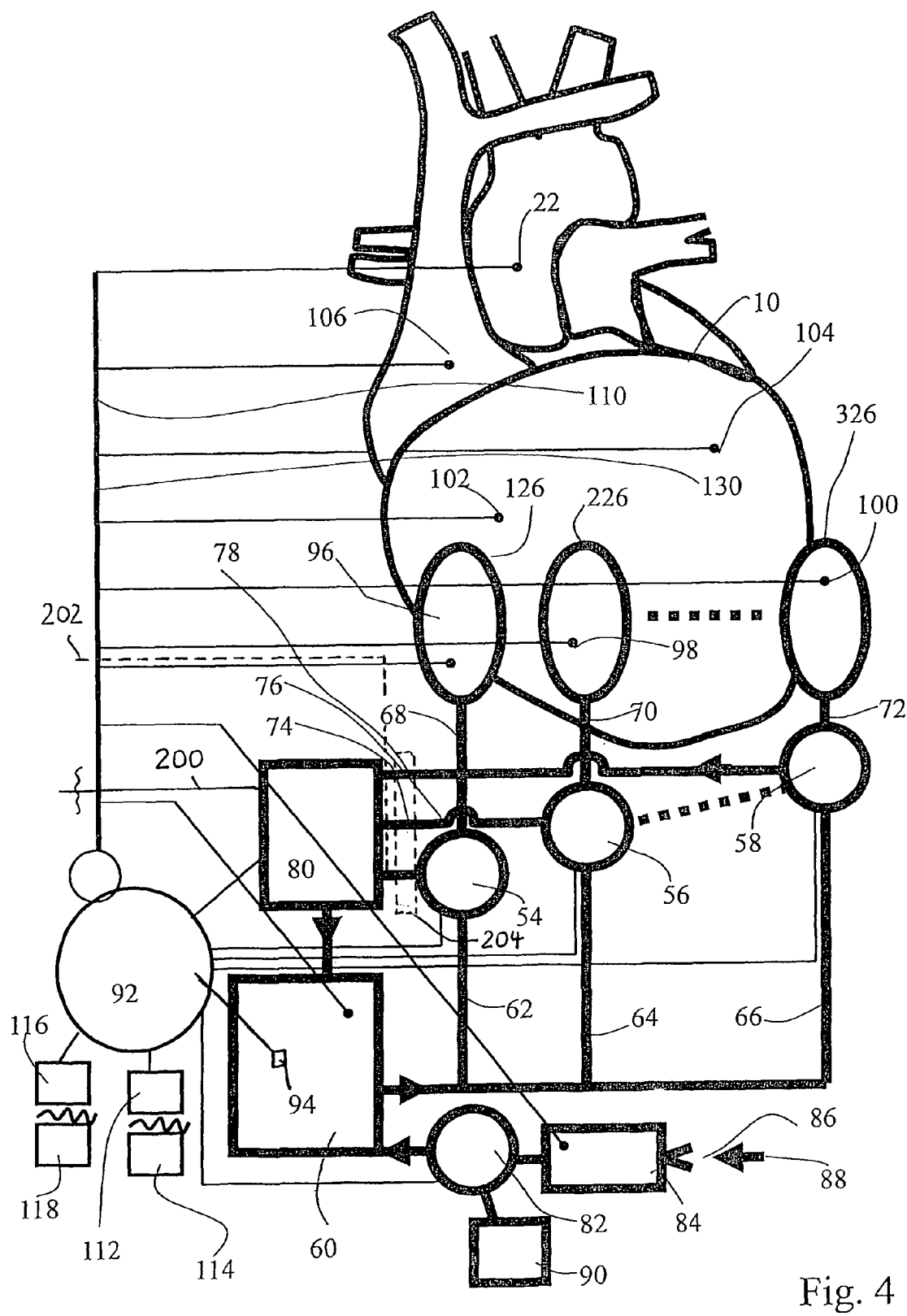
FIG. 4 shows a schematic view of the cardiac assistance device according to the preceding figures, along with the control system and pump.
Figure 5:
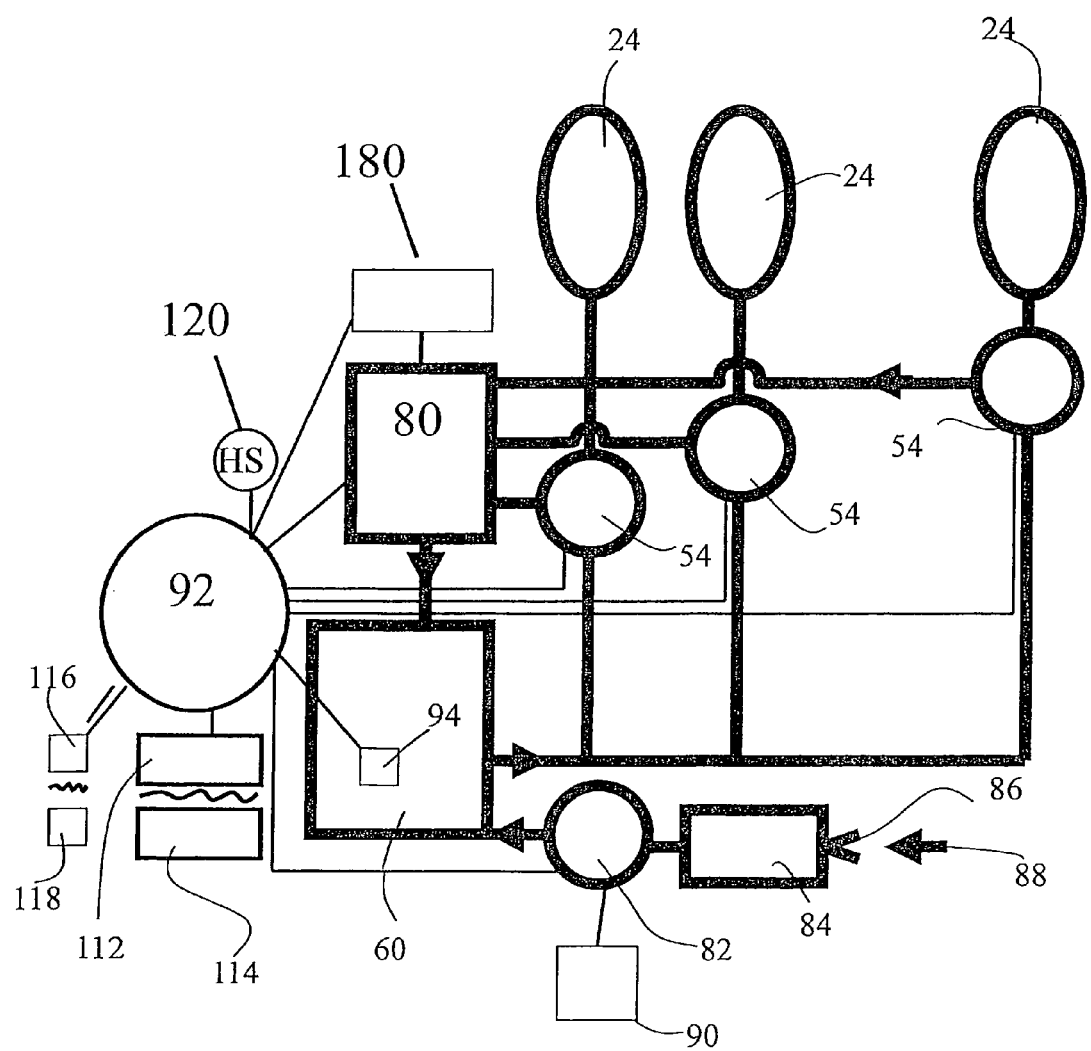
FIG. 5 shows a schematic view of a cardiac assistance device that is slightly modified in relation to FIG. 4.

The chambers 24 are part of a fluid circuit, which is shown by way of example in FIGS. 4 and 5.

The chambers 24 can be formed, for example, by means of a membrane being adhesively bonded or welded directly onto the inside of the supporting component 14, such that the chambers 24 are delimited on the inside by the membrane and on the outside by the supporting component 14.

Alternatively, the chambers 24 can of course also be defined on the inside by a dedicated wall, which is secured on the supporting component 14.

As can be seen in FIG. 1, the chambers 24 extend preferably, but not necessarily, over only a section of the circumference; that is to say, they do not extend all the way around the heart. In particular, dedicated chambers 24 are assigned to the left half 30 of the heart and to the right half 32. The chambers 24 extend obliquely upward with respect to the axis A issuing from the apex 34 of the heart, which axis A preferably extends along the cardiac septum.

The chambers 24 lying opposite each other on the circumference, and assigned respectively to the heart halves 30, 32, preferably do not overlap each other in the circumferential direction, and therefore a strip-shaped, axially extending section 36 is obtained in which no chambers 24 are present. As FIG. 1 shows, the chambers 24 are also axially separated from one another and also spaced apart from one another.

The supporting component 14 is inherently stiff and dimensionally stable. It is so stiff that it is not deformed to any appreciable extent by the pumping heart and the expanding chambers. By virtue of this inherent stiffness, it is also possible for a deformed heart, whose deformation has caused its valves to close inadequately, to be brought once again to an at least approximately normal shape. In this way, the natural closure function of the valves can be improved.

The chambers 24 are filled with and emptied of pressure fluid in a pulsed manner and, at least in the filled state, press with their inside wall 28 against the heart 10, in order to compress the latter and to assist or take over the pump function.

The support during the compression of the heart 10 takes place via the inherently stiff, stable supporting component 14. By virtue of the inherently stiff supporting component 14, the chambers 24 can be positioned at any desired location, without this necessarily leading to a total compression of the heart 10, as is the case with flexible sleeves.

The supporting component 14 has a wall thickness of 1 to 5 mm, which thickness does not have to be constant.

In this connection, FIG. 8 shows, in a somewhat exaggerated form, that the wall thickness at the bottom section 18 is greater than in the area of the upper edge 38, on which the axial holder 22 is placed. The different thicknesses result in a different stiffness of the supporting component 14, wherein the sections of different stiffnesses merge in particular continuously into one another. In the area of the upper edge 38, the supporting component 14 preferably has lower stiffness than in the area of the bottom section 18 at the apex of the heart. In this way, the upper edge 38 can be made slightly softer, which reduces the load on the heart at this location.

The stiffness of the supporting component 14 can differ in the axial and/or circumferential direction, in order to be individually adapted to the heart 10 in an optimal manner.

The different inherent stiffness can also be achieved by other measures, for example by different materials, which merge into one another, or by the different proportion of reinforcing material that can be embedded in the supporting component. This is explained in more detail below with reference to FIG. 7.

According to one embodiment, the stiffness is chosen such that, during the operation of the device, the supporting component 14 bulges out locally on the outside by a maximum of 3 mm, preferably by a maximum of 1 mm, as is shown in FIG. 1, where X indicates the extent of the bulge.

The supporting component 14 can be produced using various materials, but in particular plastic, e.g. polyamide, PTFE-coated polyamide, or PEEK.

Alternatively, the supporting component 14 can also be made of metal, in particular titanium or nitinol. However, composite components made of plastic and of metal reinforcements are also possible.

When metal is used, particular advantages can be afforded by shape-memory alloys.

Figure 7:
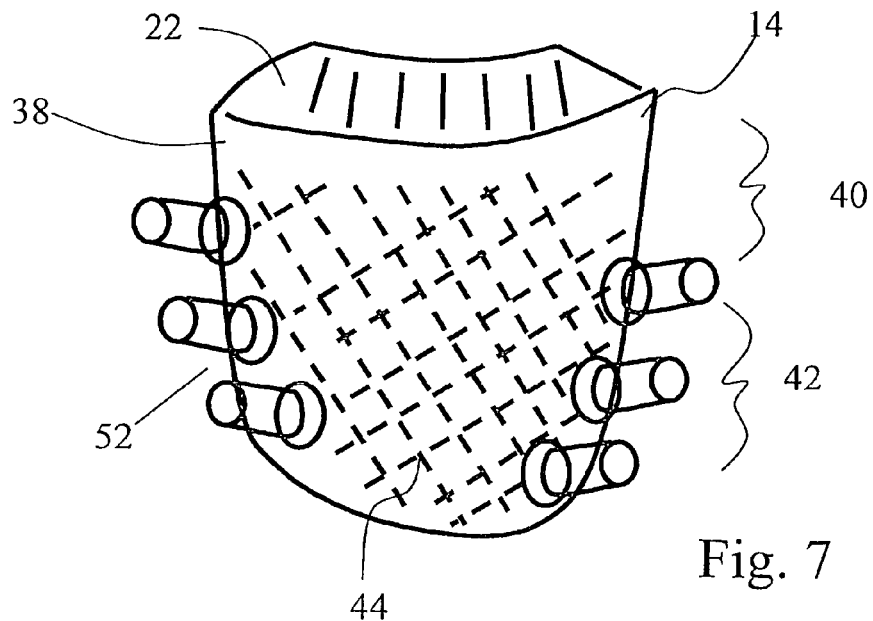
FIG. 7 shows a schematic view of part of the cardiac assistance device.

FIG. 7 shows one embodiment in which the supporting component 14 has an upper, softer area 40 and a lower, stiffer area 42.

Both areas 40, 42 are preferably dimensionally stable in relation to the normal pressure during the operation of the device. Metal reinforcements 44 are completely embedded in the plastic of the supporting component 14, for example by encapsulation. The metal reinforcements 44, here made of a shape-memory alloy, are configured in a lattice shape, in order to improve their embedding in the plastic and to permit a degree of flexibility.

Less reinforcement material in relation to the surface is present in the area 40, that is to say fewer metal reinforcements are present, in order to make the area 40 softer than the area 42 lying below it.

For the normal load during operation, the supporting component 14 should be inherently stiff. However, at higher loads, for example during heart massage or in the event of a blow against the chest, the supporting component 14 is flexible enough to permit a radial elastic compression. In the unfitted state, the elasticity is so great that the supporting component 14 is able to deform by at least 75% in relation to the unloaded state, without plastically losing shape or breaking. In FIG. 8, in this connection, the distance D between adjacent wall sections in the unloaded state is shown, and broken lines show the distance when the supporting component 14 is compressed. This distance D can be reduced to at least 75% without destroying the supporting component 14. The elasticity of the supporting component 14 can even be go great that the wall sections lying opposite each other touch (see FIG. 8), in which case, touch is also to be understood as meaning that the inner walls of the non-inflated chambers 24 touch each other.

The flexibility of the supporting component 14 does not have to be present in every section, particularly not in the area of the bottom section 18. It suffices if the upper third, in particular the upper half, has the aforementioned elasticity.

Figure 3:
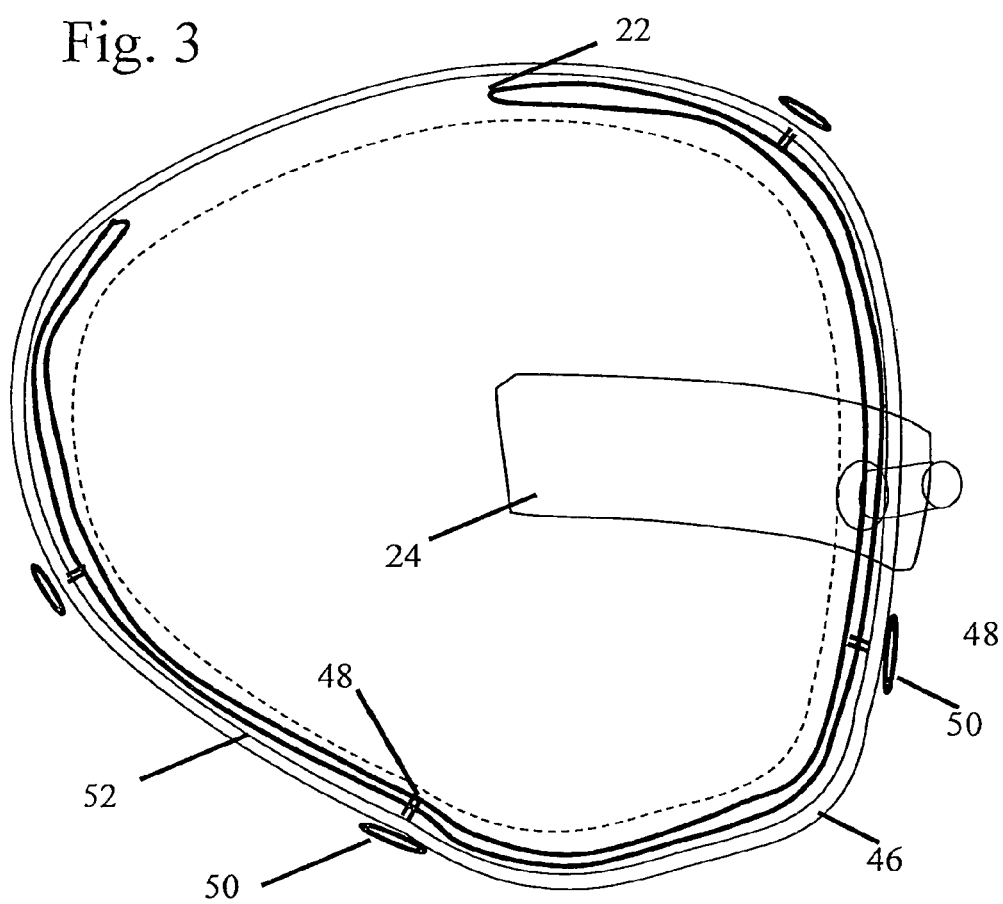
FIG. 3 shows the cardiac assistance device in a further embodiment.

To secure the position of the supporting component 14 in the body, it can be fitted into the pericardium 46 (see FIG. 3). A first fixing of its position is already achieved in this way.

In addition, fastening means can also be provided, for example fastening extensions 48 which are mounted, in particular integrally molded, on the outside of the supporting component 14 and which protrude through small openings in the pericardium 46. A closure piece 50 is placed from the outside onto the free end of the fastening extension 48, in order to avoid the fastening extension 48 sliding out. This closure piece 50 is in particular a press stud, which is placed on a correspondingly shaped end of the fastening extension 48. As can be seen in FIG. 3, a plurality of fastening extensions 48 can be mounted at any desired locations.

Alternatively or in addition to this, the supporting component 14 is sewn onto the pericardium 46, the pericardial reflection, the aorta or the pulmonary ligament. A molded-on suture holder 52, provided on the supporting component 14, can be seen particularly clearly in FIGS. 3 and 8.

In order to reduce the friction on the exterior of the heart, the unit composed of supporting component 14 and chambers 24 has, on its inside, a wall or a coating of PEEK or PTFE or other low-friction coatings/materials. For this purpose, an additional complete wall can be formed for example, which extends like a pouch inside the supporting component 14. Optionally, however, the inside walls 28 can also be designed accordingly.

The axial height of the supporting component 14, measured from the apex 34 of the heart, should be chosen such that the upper edge 38 lies approximately 10 to 20 mm below what is called the cardiac valve plane. Another definition in this context, which is likewise intended to reduce or exclude an influence of the valves, is that no chambers 24 are allowed to protrude into the valve plane. The chambers 24 should then likewise end some 10 to 20 mm below the valve plane.

Figure 2:
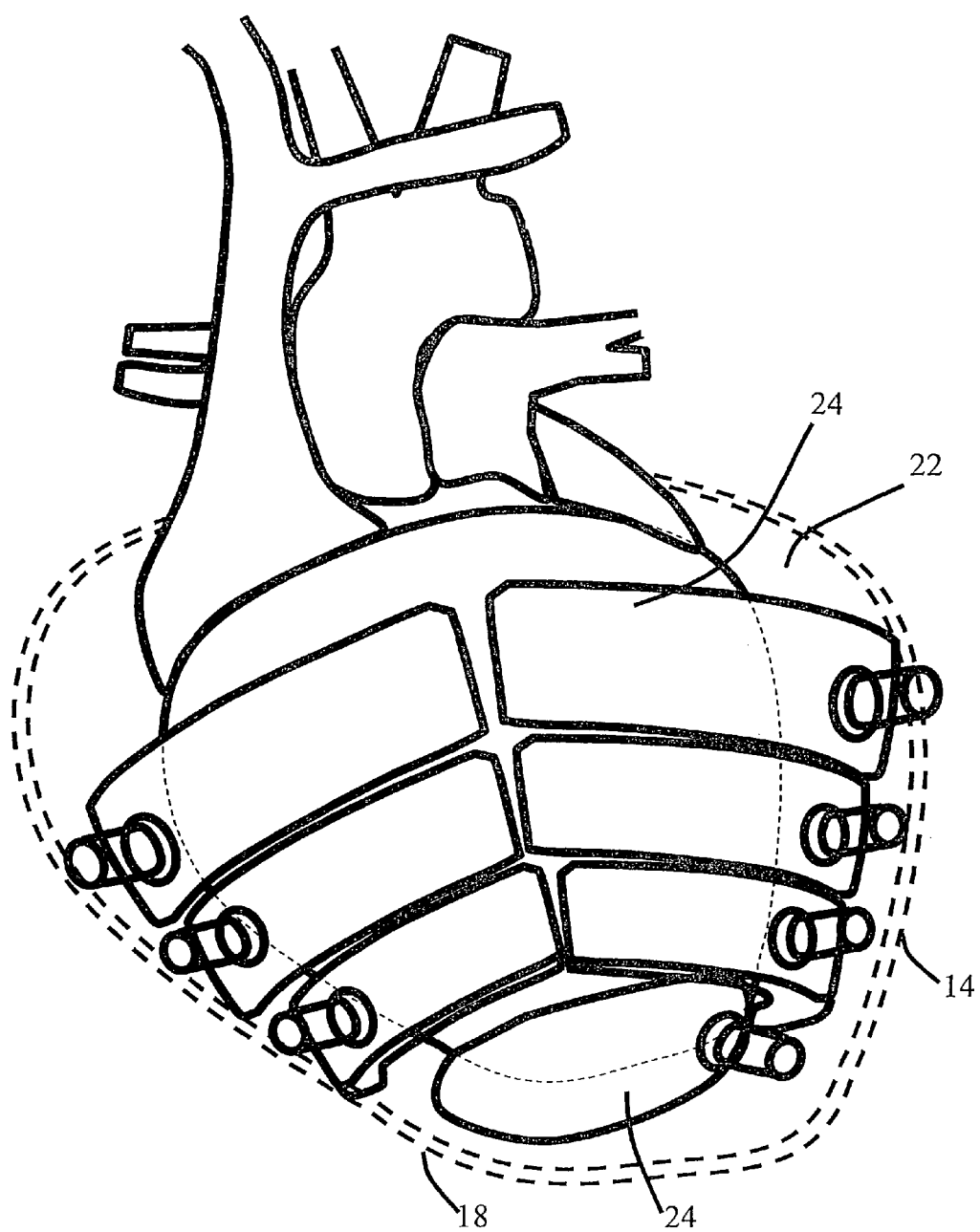
FIG. 2 shows the cardiac assistance device according to FIG. 1, with the supporting component removed.

FIG. 2 gives a better illustration of the individual chambers. In contrast to FIG. 1, the lowermost chamber 24' is designed with a greater volume and largely covers the bottom section 18. By way of this chamber 24', the axial inner height of the unit composed of supporting component 14 and chambers 24 can be varied slightly and adapted to the heart volume. The pump function can also be assisted via the chamber 24'.

FIG. 3 illustrates that in some embodiments the chambers 24 do not have to cover approximately the entire inner face of the supporting component 14. Instead, in view of the possible local weakness of the patient's heart, it is much better to provide chambers at a few individual locations. A plurality or multiplicity of chambers 24 can thus be provided, the device being preferably designed with numerous chambers 24.

FIG. 4 shows an overview of the entire cardiac assistance device, in which the unit composed of supporting component 14 and chambers is indicated symbolically by three chambers 126, 226 and 336. Some embodiments may have more than three chambers 126, 226 or 326 integrated into the overall device. Each chamber 126, 226, 326 has a fluidic connection to a pressure fluid accumulator 60 via a dedicated multi-way valve 54 to 58 assigned to the respective chamber alone. From the pressure fluid accumulator 60, lines 62 to 66 run to the valves 54 to 58. These lines 62 to 66 are supply lines. Lines 68 to 72 between the valves 54 to 58 and the chambers 126 to 326 are combined supply and discharge lines.

From the valves 54 to 58, which serve as combined supply and discharge valves, discharge lines 74 to 78 run to a fluid pump 80, which pumps fluid into the accumulator 60.

In some embodiments, instead of the combined supply and discharge lines 68 to 72, it is also possible for separate supply and discharge lines to lead to and from the chambers 126 to 326.

The pump 80 preferably works permanently and generates a permanent pressure in the accumulator 60. The accumulator 60 in turn has a fluidic connection to an intracorporeal fluid refill tank 84 via a refill tank valve 82. The fluid refill tank 84 contains fluid (preferably pressurized), which flows into the above-described fluid circuit via the temporarily opened valve 82 when there is too little fluid in the circuit.

The refill tank is preferably made of metal (in particular titanium), plastic or glass, or of a sandwich structure made of these materials.

Alternatively or in addition to the fluid refill tank 84, a transcutaneously connectable refill interface 86 is provided, which is designed in particular as a passive valve and is accessible from the outside, for example via a syringe 88. In this way, if there is a lack of fluid in the circuit, more fluid can be introduced from the outside. The interface 86 can also be coupled directly to the accumulator 60.

The coupling of the refill tool (here a syringe) can be effected, for example, by a rotary (i.e. screw) fastening or bayonet catch.

The refill tank valve 82 can be controlled either via a dedicated control system 90 or via a central control system 92. The control system 90 can, for example, also be controlled from outside the body via transmitter and receiver units, in order to temporarily open the refill tank valve 82. The amount of the fluid supplied is also controlled by the opening time of the refill tank valve 82.

The control system 90 or 92, which is responsible for the refill tank valve 82, is configured in such a way that, if there is a fluid loss in the fluid circuit, it automatically drives the refill tank valve 82. However, as has already been explained, this control can also be effected from outside the body.

A pressure sensor 94 in the accumulator 60 is connected to the control system 92 and provides information concerning the pressure in the accumulator 60. The control system 92, described below as the central control system, has a connection to the pump 80, to the individual valves 54 to 58, if appropriate to the refill tank valve 82, and also to sensors 96 to 100, which are accommodated in the chambers 126 to 326. In this way, the pressure in the chambers 126 to 326 can be determined. Further pressure sensors 102, 104 detect the pressure in the two heart chambers, and pressure sensors 106 to 108 in the vein and the aorta, respectively.

In addition to or as an alternative to the pressure sensors 102 to 104, the central control system 92 can also be coupled to an ECG sensor 130 and/or to a pacemaker, such as a twin-chamber pacemaker 110. The pump 80 can be connected directly, or via the central control system 92, to an energy store 112, such as a battery. In particular, without having to pass lines through the skin, this energy store 112 can be permanently or temporarily charged from the outside via a magnetic or electric transmitter 114. The central control system 92 can be controlled from the outside, likewise via transmitter/receiver unit 116, 118, or could also be reprogrammed. In addition, the transmitter/receiver unit 118 provided outside the body can also be coupled to an Internet interface, in particular via wireless LAN. It is thus possible for the patient to be connected as it were from home to a physician, so that the latter can read out the patient's values and, if appropriate, reprogram the central control system 92.

During operation, the pump 80, preferably designed with a brushless drive, ensures a permanent overpressure in the pressure fluid accumulator 60. The central control system 92 drives the valves 54 to 58 individually, such that pressure fluid from the accumulator 80 inflates the chambers 126 to 326 in a pulsed manner and thus contracts the heart 10. The chambers 126 to 326 are driven independently, either individually or in groups, via the valves 54 to 58 (individually according to FIG. 4). After the compression of the heart 10, the valves 54 to 58 are reversed under pressure control and/or ECG control, such that the chambers 126 to 326 are connected fluidically to the pump 80 and are abruptly emptied. The heart 10 can thus expand again.

The extent of the compression of the heart 10 can depend on the pressure or flow values determined by the sensors.

As has been shown, the device can be designed as a closed circuit, which lies completely inside the body or which is also positioned partially outside the body (e.g. pump or energy store).

In another embodiment of the invention, provision is made for the device to be operated as an open system. This means that the device, downstream of the chambers, releases the compressed air outside the body via a line protruding from the body. If they are present, the discharge valves can still be located inside the body. The pump lying inside or outside the body sucks in air from the atmosphere. In this connection, a suction line 200 leading to the atmosphere is shown by broken lines in FIG. 4. The lines 74, 76, 78 would in this case not connect to the pump 80, and instead they would lead outside the body via a collecting line 202.

In addition to or as an alternative to the pressure accumulator 60, a pressure fluid collection chamber 204 (broken line in FIG. 4) can also be present upstream from the pump, and the lines coming from the individual chambers open into this pressure fluid collection chamber 204. The pressure fluid collection chamber serves as an intermediate store for fluid.

The cardiac assistance device is equipped with an emergency sensor system, which utilizes the sensors 96 to 100. As soon as the control system 92 detects an excessive drop in pressure in one of the chambers 126 to 326, the corresponding valve 54 to 58 is permanently closed, such that no more fluid can flow out via the defective chamber.

Moreover, the control system 92 is configured in such a way that it changes the speed of rotation of the pump 80 when the pressure in the pressure accumulator drops below a predefined minimum pressure or exceeds a predefined maximum pressure or if the pulse rate is high.

In some circumstances, the heart 10 assisted by the device may become smaller over the years. This means that the device possibly provides less assistance and/or that the fit of the unit composed of supporting component 14 and chambers 126 to 326 may deteriorate. As soon as this decrease in size of the heart 10 is detected, the control system 92 can drive the valves 54 to 58 in such a way that the chambers 126 to 326 are emptied less completely, that is to say that they bear constantly on the heart wall. In addition to or as an alternative to this, hitherto unused chambers, for example the chamber 24' shown in FIG. 2, can be filled or can be more completely filled.

One possible way of detecting a decrease in size of the heart is to infer this from a constantly reduced chamber pressure and/or blood pressure. The chambers 126 to 326 do not have to be filled simultaneously. Instead, it is sometimes advantageous for them to be filled and then emptied again at a time interval between each other. For example, the left-hand chambers (with reference to FIG. 2) can be filled slightly before the right-hand chambers 24, with the result that the left half of the heart experiences an outer pressure prior to the right half of the heart.

It is also possible for the chambers 24 to be filled in a slightly staggered manner starting from the apex 18 of the heart, such that the uppermost chambers 24 are filled last. The chronologically staggered inflation procedure from the lowermost chamber 24 to the uppermost chamber 24 is intended to ensure the so-called lifting function of the heart in the direction of the aorta.

The pressure in the chambers 24, 126 to 326 or in the heart halves also provides information on the function and the performance of the heart. By means of pressure values, which are determined via pressure sensors, and by means of pressure profiles, a functional evaluation of the heart can be calculated and, if appropriate, represented three-dimensionally. A healthy heart has less counter-pressure, such that less fluid also has to be introduced into the chambers 24, 126 to 326. Should the heart recover in terms of its performance, a lower pressure is then likewise generated in the chambers 24, 126 to 326 via the control system 92.

As explained above on the basis of FIGS. 1 to 3, the size, number, position and volume of the chambers 24, 126 to 326 can vary, in order to adapt the device to the heart disease and to the size of the heart.

The embodiment according to FIG. 5 corresponds substantially to the one according to FIG. 4, for which reason only the differences are explained below.

In this embodiment, in addition to the pump 80, there is also an emergency pump 180 coupled to the latter. As soon as the pump 80 fails, the emergency pump 180 is switched on via the control system 92 and then ensures the necessary pressure in the fluid. In addition to or as an alternative to the previous sensors, so-called trigger sensors 120 are also provided, via which coordination can take place between the heart function and the pump function of the device.

Figure 6:
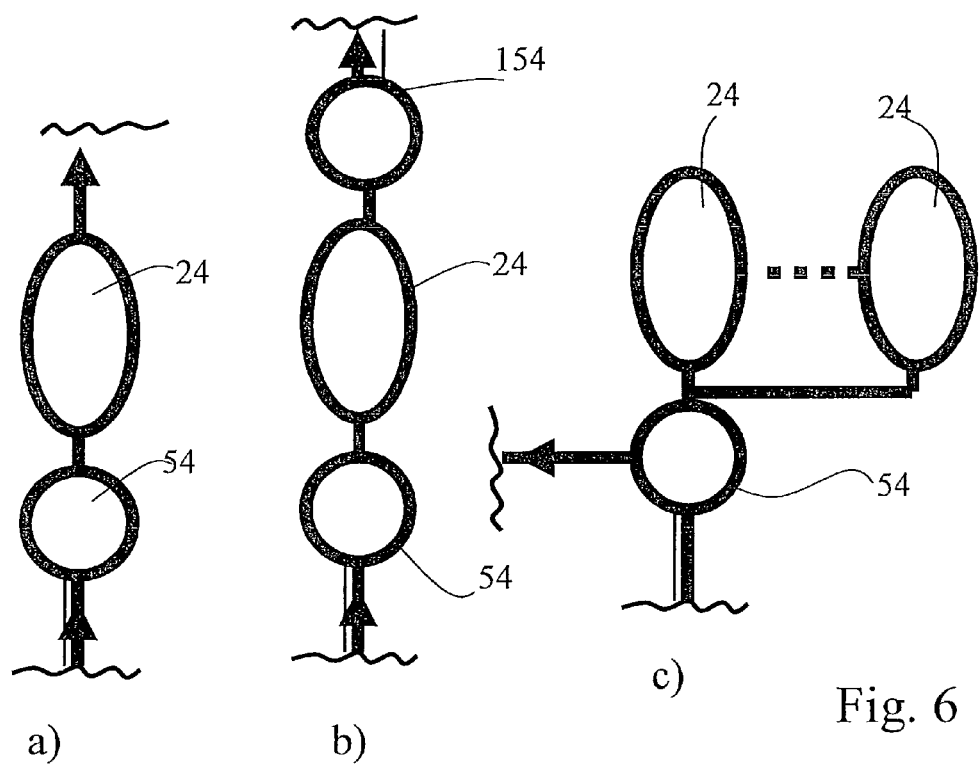
FIGS. 6a to 6c show schematic views of the valve circuits that can be used in the device.

FIG. 6 shows various other embodiments of how the chambers 24, 126 to 326 are controlled.

In the embodiment according to FIG. 6a, a permanent discharge is provided, such that only the valve 54 is responsible for the pressure build-up in the chamber 24.

In the embodiment according to FIG. 6b, separate inlet and outlet valves 54, 154 are provided.

In the embodiment according to FIG. 6c, a plurality of chambers 24 are controlled via a common valve, here a combined supply and discharge valve 54.

The production of the supporting component 14 is explained in more detail below. The supporting component 14 is specially adapted to the shape of the patient's heart 10 and is produced individually. This production takes place as a three-dimensional tailored production. For this purpose, data concerning the heart are obtained by an MRT and/or CT scanning method (see FIG. 9). This data set may directly or indirectly provide information on cardiac geometry (e.g., three-dimensional outer shape of the heart or outer shape of the pericardium). Indirectly means that data determined by the MRT or CT are used to calculate the corresponding data for the 3D shape of the heart (surface reconstruction; surface rendering). These data are input directly, or via a data memory 122, into a control system 124 of a machining center 128. In the machining center 128, these data are implemented fully automatically in order either to simulate the heart or directly produce the supporting component 14. The machining center 126 is, for example, a center for laser sintering, stereolithography or the like. Alternatively, it can also be a material-removal machining center.

In this connection, it would be possible, for example, to use the resulting 3D shape in order to select, from a large number of prefabricated supporting components, a supporting component 14 that requires less finishing work than the others. The machining center 128 could, for example, be a milling machining center, via which the fine tuning then takes place.

As a further alternative, it would be possible that the machining center 128 produces one or more elements of an injection mold 130 (see FIG. 10). The supporting component 14 is then cast using this injection mold 130 (see FIG. 10), in which a male mold 132 has been produced individually.

Using the patient specific cardiac data obtained by the CT or MRI method and from which the 3D shape of the heart can be determined, it is also possible to match the size and the position of the chambers 24, 126 to 326 exactly to the situation.

A combination of the individually controllable chambers 24, 126 to 326 with a twin-chamber pacemaker system serves for resynchronization of the heart activity.

Instead of being fitted in the inside of the pericardium, the supporting component 14 can also sit on the outside of the pericardium and surround the latter. All of the aforementioned features can also be used accordingly in this alternative.

The method just described may also be employed for the production of an implant that completely or partially replaces an internal organ or an internal organ structure, or that is implanted adjoining the latter, in order to assist the organ. This implant is produced individually on the basis of data obtained by an imaging method and reproducing the three-dimensional organ shape or the body part replaced by the implant. The implant does not replace a hard body part, such as a tooth or a bone, but replaces or assists a soft body part in the interior of the body. Accordingly, the contour of a soft body part in the interior of the body is determined by the imaging method in order to be able to produce a patient-specific implant.

In some embodiments, the implant is the aorta, which includes aortic bifurcations (ascending, arch, descending), or a heart valve or a supporting component adjoining and supporting the diaphragm or the lung.

Laser sintering is particularly preferably employed in this method, in which case the materials used are the materials or sandwich materials mentioned above and below.

The cardiac assistance device is preferably a pneumatically operating device, i.e. the chambers are inflated using gas, in particular air.

The invention claimed is:

1. A cardiac assistance device comprising:
a supporting component configured to surround a heart and having an inside wall arranged to face the heart;
a plurality of inflatable chambers disposed within the supporting component and arranged to displace respective regions of the inside wall of the supporting component toward the heart when inflated;
a fluid circuit comprising a pump having an inlet and an outlet, and a plurality of combined supply and discharge valves, each valve fluidly connecting the pump inlet and outlet to a respective subset of inflatable chambers, the valves being independently operable to control the supply and discharge of fluid to their respective subset of the inflatable chambers, and
an intracorporeal fluid refill tank connected to the fluid circuit via a refill tank valve that allows fluid to flow from the refill tank into the fluid circuit when opened.

2. The device of claim 1, wherein the fluid circuit further comprises an accumulator disposed between the pump and the inflatable chambers, such that fluid is fed from the pump into the accumulator.

3. The device of claim 2, further comprising a pressure sensor responsive to pressure in the accumulator.

4. The device of claim 3, further comprising a control system coupled to the pressure sensor and configured to increase speed of rotation of the pump when the pressure in the pressure accumulator reaches a predefined pressure threshold.

5. The device of claim 1, wherein the fluid circuit further comprises at least one fluid collection chamber disposed downstream of the inflatable chambers,
such that fluid flows from the inflatable chambers back to the pump through the fluid collection chamber.

6. The device of claim 1, wherein the fluid circuit includes a respect supply line to each inflatable chamber.

7. The device of claim 6, wherein each inflatable chamber has a discharge side directly connected to the pump.

8. The device of claim 1, further comprising:
a valve control system operably connected to the valves; and
an emergency sensor system responsive to chamber leakage detection and configured to permanently close the valve associated with an inflatable' chamber from which leakage is detected.

9. The device of claim 1, further comprising an emergency pump and a pump control system configured to activate the emergency pump in response to detection of as defect of the pump of the fluid circuit.

10. The device of claim 1, further comprising
a plurality of pressure sensors configured to emit pressure signals indicative of chamber or blood pressure; and
a central control system operably connected to the valves and pump and responsive to the pressure signals, the central control system configured to operate the valves to empty their respective subsets of inflatable chambers to a lesser degree in response to a signal indicating a constantly reduced pressure.

11. The device of claim 1, wherein the refill tank valve is configured to be operable from outside the body containing the heart.

12. The device of claim 1, wherein the refill tank valve is configured to automatically open in response to a loss of fluid in the fluid circuit.

13. The device of claim 1, wherein the fluid circuit further comprises a transcutaneously connectable refill interface releasably couplable to a refill tool connectable from the outside the body containing the heart.

14. The device of claim 1, further comprising a central subcutaneous control system operably connected to the pump and the valves, the control system including at least one of
a receiver via which the control system is reprogrammable; and
a transmitter to transmit data from the device.

15. The device of claim 14, wherein the transmitter transmits wirelessly.

16. The device of claim 1, wherein at least one of the respective subsets of the inflatable chambers consists of a single inflatable chamber.

17. A cardiac assistance device comprising:
a supporting component configured to surround a heart and having an inside wall arranged to face the heart;
a plurality of inflatable chambers disposed within the supporting component and arranged to displace respective regions of the inside wall of the supporting component toward the heart when inflated;
a fluid circuit comprising a pump and a plurality of supply valves, each valve connecting the pump to a respective subset of inflatable chambers, the valves being independently operable to control their respective subset of the inflatable chambers;
an intracorporeal fluid refill tank connected to the fluid circuit via a refill tank valve that allows fluid to flow from the refill tank into the fluid circuit when opened; and
wherein the fluid circuit is an open system and each inflatable chamber has a discharge side vented to atmosphere.

18. The device of claim 17 wherein the pump draws atmospheric air.

* * * * *

UNITED STATES PATENT AND TRADEMARK OFFICE
CERTIFICATE OF CORRECTION

PATENT NO. : 8,944,987 B2
APPLICATION NO. : 13/393420
DATED : February 3, 2015
INVENTOR(S) : Markus Meister and Stephen Wildhirt Page 1 of 1

It is certified that error appears in the above-identified patent and that said Letters Patent is hereby corrected as shown below:

In the Specification:

Column 1, line 9, delete "EP2010/005947." and insert -- EP2010/005947, --, therefore.

In the Claims:

Column 12, line 50, claim 1, before "inflatable" insert -- the --, therefore.

Column 12, line 53, claim 1, delete "chambers, and" and insert -- chambers; and --, therefore.

Column 13, line 7, claim 6, delete "respect" and insert -- respective --, therefore.

Column 13, line 15, claim 8, delete "inflatable'" and insert -- inflatable --, therefore.

Column 13, line 19, claim 9, delete "as" and insert -- a --, therefore.

Signed and Sealed this
Second Day of June, 2015

Michelle K. Lee
*Director of the United States Patent and Trademark Office*